United States Patent [19]
Masuda et al.

[11] Patent Number: 5,527,801
[45] Date of Patent: Jun. 18, 1996

[54] AMELIORANT FOR BLOOD LIPID METABOLISM

[75] Inventors: Yoshinobu Masuda, Katano; Hisao Minato, Sanda; Akihisa Ikeno, Osaka; Kunihiko Takeyama, Ikoma; Kanoo Hosoki, Toyonaka, all of Japan

[73] Assignee: Dainippon Pharmaceutical Co., Ltd., Osaka, Japan

[21] Appl. No.: 204,430

[22] PCT Filed: Sep. 14, 1992

[86] PCT No.: PCT/JP92/01173

§ 371 Date: Mar. 14, 1994

§ 102(e) Date: Mar. 14, 1994

[87] PCT Pub. No.: WO93/05778

PCT Pub. Date: Apr. 1, 1993

[30] Foreign Application Priority Data

Sep. 24, 1991 [JP] Japan .................................. 3-273319

[51] Int. Cl.$^6$ .................................................. A61K 31/495
[52] U.S. Cl. .......................... 514/255; 544/359; 549/12
[58] Field of Search .............................................. 514/255

[56] References Cited

U.S. PATENT DOCUMENTS 4,749,703   6/1988   Uno et al. .

FOREIGN PATENT DOCUMENTS 61-47466   3/1986   Japan .
3-72425    3/1991   Japan .
86/01203   2/1986   WIPO .

OTHER PUBLICATIONS

Triggle, D. J. et al., "Calcium Antagonists", *Drug News Perspective*, vol. 4, No. 10, Dec. 1991, pp. 643–646.

Minato, H. et al., "Inhibitory Effect of the New Calcium Antagonist AJ–2615 on Progression of Atherosclerosis in Cholesterol–fed Rabbits", *Journal of Cardiovascular Pharmacology*, vol. 21, No. 4, 1993, pp. 663–669.

Minato, H. et al., "Preventive Effect of AJ–2615; A Novel Calcium Entry Blocker, On the Development of Experimental Atherosclerosis in Rabbits", *5th International Symposium on Calcium Antagonists: Pharmacology and Clinical Research*, 1991, p. 91.

*Drugs of the Future*, vol. 17, No. 4, 1992, pp. 314–315.

Cubeddu, L. X. et al., "Effect of Doxazosin Monotherapy on Blood Pressure and Plasma Lipids in Patients with Essential Hypertension", *American Journal of Hypertension*, vol. 1, No. 2, 1988, pp. 158–167.

Bernini et al. (1989) "Effects of Calcium Antagonists on Lipids and Antherosclerosis" *Am. J. Cardiology.*, 64, 129–134.

Ginsburg et al. (1983) "Calcium Antagonists Suppress Atherogenesis in Aorta but Not in the Intramural Coronary Arteries of Cholesterol–Fed Rabbits", *Laboratory Investigation*, 49:154–158.

Handa et al. (1983) "Report of Use of Prazosin Hydrochloride—as to Hypotensive Activity and Effects on Blood Lipids", *Prog. Medicine*, 3:1517–1525.

Lowenstein et al. (1984) "Effects of Prazosin and Propranolol on Serum Lipids in Patients with Essential Hypertension", *Am. J. Medicine*, 76:79–84.

Naito et al. (1984) "Ineffectiveness of $Ca^{2+}$–Antagonists Nicardipine and Diltiazem on Experimental Atherosclerosis in Cholesterol–fed Rabbits", *Atherosclerosis*, 51:343–344.

Okamura et al. (1990) "Effect of a novel $Ca^{2+}$ entry blocker, AJ–2615 in isolated vascular smooth muscles"; *Jpn. J. Pharmacol.*, 52, (Suppl. 1):212 (Abstract No. P067).

Primary Examiner—Paul J. Killos
Attorney, Agent, or Firm—Scully, Scott, Murphy & Presser

[57]   ABSTRACT

The present invention is to provide an ameliorant for blood lipid metabolism which comprises as an active ingredient N-(6,11-dihydrodibenzo[b,e]thiepin-11-yl)-4-(4-fluorophenyl)-1-piperazinebutanamide or a pharmaceutically acceptable salt thereof, more particularly, to provide a hyperlipidemia inhibitor and an atherosclerosis inhibitor.

18 Claims, 1 Drawing Sheet

Normal

Positive Control

Salt of Compound A

Prazosin

Diltiazem

AMELIORANT FOR BLOOD LIPID METABOLISM

This application is a 371 of PCT/JP92/01173 Sep. 14, 1992.

TECHNICAL FIELD

The present invention relates to a useful and novel agent as a medicine. Particularly, the present invention relates to a novel use of a specific dibenzo[b,e]thiepine derivative. That is, the present invention relates to an ameliorant for blood lipid metabolism, which comprises as an active ingredient a dibenzob[b,e]thiepine derivative of the following structural formula (hereinafter, referred to as Compound A), or a pharmaceutically acceptable salt thereof, more particularly, the present invention relates to a hyperlipidemia inhibitor and an inhibitor of atherosclerosis in the aorta, and a method for ameliorating blood lipid metabolism.

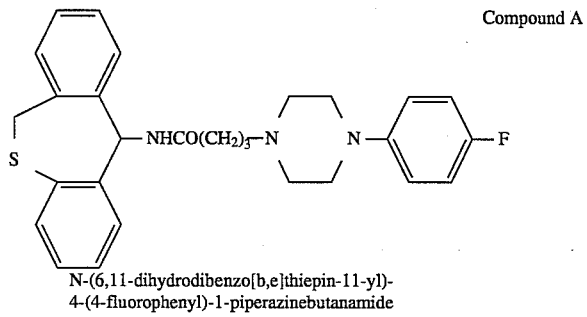

N-(6,11-dihydrodibenzo[b,e]thiepin-11-yl)-
4-(4-fluorophenyl)-1-piperazinebutanamide It has been already disclosed in Japanese Patent Second Publication (Kokoku) No. 58341/1991 (U.S.Pat. No. 4,749,703) that Compound A of the present invention and salts thereof have a potent calcium antagonistic activity and are useful as a hypotensive agent. Besides, it has also been disclosed in Jpn. J. Pharmacol., 52 (suppl. 1), 212 (No. P067) (1990) that Compound A and salts thereof have $\alpha_1$-receptor blocking activity.

In Am. J. Cardiology 64, 129 1-134 1 (1989), there is an introduction of many reports as to the hyperlipidemia inhibitory activity and the atherosclerosis inhibitory activity of various calcium antagonists, wherein it is described that the antagonists did not show any hyperlipidemia inhibitory activity in most of the reports and that as to atherosclerosis inhibitory activity the antagonists showed positive activity in some reports but did not in other reports.

Moreover, it is reported that diltiazem, which is a benzothiazepine derivative and a well known hypotensive agent having calcium antagonistic activity, shows the atherosclerosis inhibitory activity in rabbits [Lab. Invest., 49 (2), 154–158 (1983)], and on the contrary, there is a report of having no inhibitory activity [Atherosclerosis, 51, 343–344 (1984)].

Besides, it is reported that prazosin, which is a benzopyrimidine derivative being well known as a hypotensive agent having $\alpha_1$-receptor blocking activity, shows blood lipid decreasing activity in human being [Am. J. Medicine, 76 (suppl. 2A), 79–84 (1984)], and on the contrary, there is a report of having no blood lipid decreasing activity [Prog. Medicine 3, 1517–1525 (1983)].

DISCLOSURE OF INVENTION

The present inventors have found that the above Compound A shows the hyperlipidemia inhibitory activity as well as the atherosclerosis inhibitory activity at a dose effective for showing hypotensive activity, and that they are useful as an ameliorant for blood lipid metabolism, more particularly, as a hyperlipidemia inhibitor and atherosclerosis inhibitor, and have accomplished the present invention.

That is, an object of the present invention is to provide an ameliorant for blood lipid metabolism which comprises as an active ingredient Compound A or a pharmaceutically acceptable salt thereof. More particularly, the object of the present invention is to provide a hyperlipidemia inhibitor and atherosclerosis inhibitor.

BEST MODE FOR CARRYING OUT INVENTION

Figure 1A:
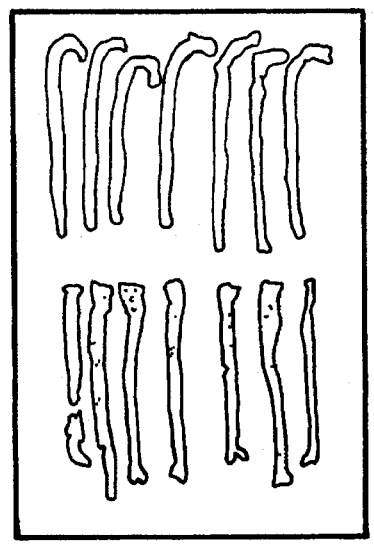
FIG. 1 shows the appearances of lipid deposition at the aortic inner wall. Each figure shows the appearances of lipid deposition, i.e. the appearances of plaque formation in the following groups, (a): the normal control group (normally fed);(b): the positive control group (fed with high fat feed); (c): maleate of Compound A-treated group; (d): the prazosin-treated group; and (e): the diltiazem-treated group.

The present inventors have firstly found that the above mentioned Compound A and a pharmaceutically acceptable salt thereof inhibit the increase in blood lipid at a dose effective for showing hypotensive activity (hyperlipidemia inhibitory activity) as well as inhibit the lipid deposition at the aortic inner wall (atherosclerosis inhibitory activity), by which they are useful as an ameliorant for blood lipid metabolism, and have accomplished the present invention.

The pharmaceutically acceptable salt of Compound A of the present invention includes, for example, salts with an inorganic acid (e.g. hydrochloride, hydrobromide, hydroiodide, sulfate, phosphate, etc.) and salts with an organic acid (e.g. oxalate, maleate, fumarate, malate, citrate, benzoate, methanesulfonate, etc.). Among them, the maleate is more preferable. Besides, Compound A and a pharmaceutically acceptable salt thereof may be in the form of a hydrate or solvate, or in the form of optically active compound.

The safety of Compound A and a pharmaceutically acceptable salt thereof in the living body is already proved and confirmed, for example, the acute toxicity ($LD_{50}$) in oral administration of the maleate of Compound A in mice (Jcl. ICR) is more than 500 mg/kg, and no significant toxicity was observed in rats and beagles even by prolonged administration.

Compound A and a pharmaceutically acceptable salt thereof may easily be prepared according to the disclosure of U.S. Pat. No. 4,749,703, for example, according to the disclosure of Example 1 thereof.

The agent of the present invention may be administered either orally or parenterally such as intrarectally, but oral administration is preferable. The daily dosage of the present agent varies according to the administration routes and the conditions and ages of patients, but it is usually in the range of 0.01 to 5 mg of Compound A per 1 kg of body weight, preferably in the range of 0.1 to 3 mg of Compound A per 1 kg of body weight, more preferably in the range of 0.5 to 2 mg of Compound A per 1 kg of body weight, and the compound of the present invention is administered at one time, or dividedly for several times per day. At this dosage, Compound A and a pharmaceutically acceptable salt thereof show not only the ameliorating activity of blood lipid metabolism but also hypotensive activity.

The agent of the present invention may usually be in the form of tablets, capsules, granules, fine granules, powders, syrups, suspensions, injections, suppositories, and the like. The carriers incorporated with these pharmaceutical forms may be any conventional ones which do not react with Compound A and a pharmaceutically acceptable salt thereof, for example, lactose, glucose, mannitol, dextrin, starch, white sugar, crystalline cellulose, low-substituted hydroxypropyl cellulose (L-HPC), low-viscosity hydroxypropyl cellulose (HPC-L), hydroxypropyl methylcellulose (HPMC), light silicic anhydride, polyvinyl-pyrrolidone, talc, sorbitan fatty acid ester, macrogol, wax, water, and the like.

These pharmaceutical preparations may contain Compound A or a pharmaceutically acceptable salt thereof in an amount of more than 0.5%, preferably 1 to 85%, and may contain other pharmaceutically active compounds, if necessary.

The pharmacological activity of the present agent is illustrated by Experiment in comparison with diltiazem; a calcium antagonist, and prazosin; an $\alpha_1$-receptor blocking agent.

Experiment

In this experiment, male white Japanese rabbits (5 to 7 rabbits/group) were used. The high fat feed was prepared by adding 1% cholesterol and 6% coconut oil to the solid feed (Oriental Yeast Co., Ltd., RC-4). Each rabbit was fed with the high fat feed in an amount of 100 g every day, and two weeks later, the total plasma cholesterol of each rabbit was determined and confirmed to be more than 1000 mg/dl, and the rabbits were divided into two groups.

In one group, 0.5% tragacanth solution (vehicle, control) were administered to the rabbits, and in other groups, the maleate of Compound A, diltiazem or prazosin was administered orally once a day for 9 weeks. The dosages of the maleate of Compound A, diltiazem and prazosin were 30 mg/kg/day, 50 mg/kg/day and 3 mg/kg/day, respectively, and at these dosages, these compounds show hypotensive activity as well.

Separately, in the normal feed group, each rabbit was given normal solid feed (RC-4) (100 g/day) and a vehicle (tragacanth solution) orally.

Six, eight and nine weeks after the beginning of administration, the total cholesterol, free cholesterol and phospholipid in plasma were determined, and the results are shown in the following Tables 1 to 3.

Figure 1B:
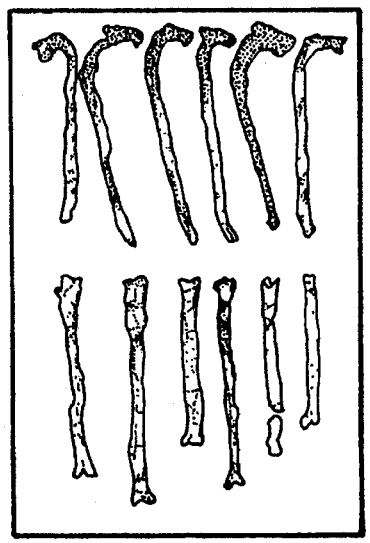
Figure 1C:
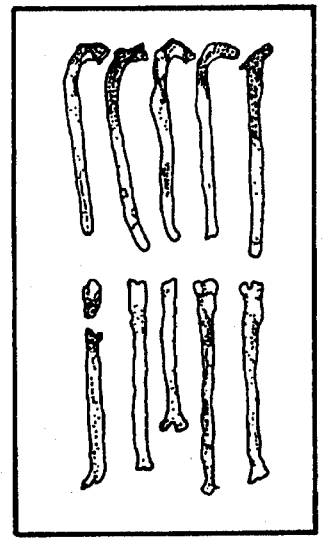
Figure 1D:
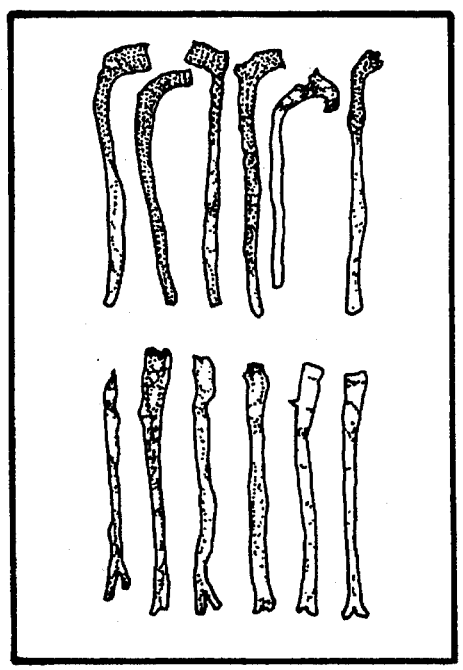
Figure 1E:
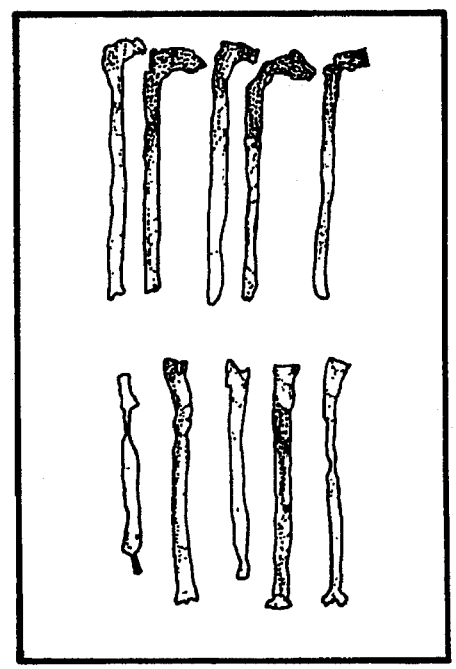

Nine weeks after the beginning of administration, each rabbit was killed with bleeding under pentobarbital-anesthesia, and the aorta was taken out. The cholesterol amount in the aorta was determined, and the lipid deposition at the aortic inner wall was stained and the area of the stained parts was measured. The results are shown in the following Table 4 and FIG. 1.

TABLE 1

Cholesterol concentration in plasma

| Tested Groups | Total cholesterol concentration in plasma (mg/dl ± standard error) Test Period (weeks) | | | |
|---|---|---|---|---|
| | 0 | 6 | 8 | 9 |
| Normal feed + Vehicle | 25 ± 2** | 27 ± 4** | 18 ± 2** | 28 ± 4** |
| High fat feed + Vehicle | 1070 ± 139 | 2279 ± 289 | 1918 ± 227 | 2106 ± 320 |
| High fat feed + Compound A*** | 1161 ± 110 | 1595 ± 136 | 1074 ± 162* | 1070 ± 171* |
| High fat feed + diltiazem | 1127 ± 202 | 2297 ± 127 | 2106 ± 293 | 1626 ± 221 |
| High fat feed + prazosin | 1201 ± 45 | 3048 ± 236 | 2082 ± 194 | 1999 ± 317 |

*Significantly different from [High fat feed + Vehicle] group ($p < 0.05$)
**Significantly different from [High fat feed + Vehicle] group ($p < 0.01$)
***The maleate of Compound A As shown in Table 1, the total cholesterol concentration was significantly decreased from 8 weeks after the beginning of administration in the maleate of Compound A-treated group. On the other hand, no decrease in the total cholesterol concentration in diltiazem-treated group and prazosin-treated group was observed even at 9 weeks after the beginning of administration.

TABLE 2

Free cholesterol concentration in plasma

| Tested Groups | Free cholesterol concentration in plasma (mg/dl ± standard error) Test Period (weeks) | | | |
|---|---|---|---|---|
| | 0 | 6 | 8 | 9 |
| Normal feed + Vehicle | 8 ± 1** | 10 ± 1** | 8 ± 1** | 5 ± 1** |
| High fat feed + Vehicle | 349 ± 38 | 746 ± 85 | 607 ± 79 | 672 ± 140 |
| High fat feed + Compound A*** | 346 ± 34 | 503 ± 43 | 330 ± 56* | 306 ± 39* |
| High fat feed + diltiazem | 318 ± 57 | 660 ± 42 | 673 ± 96 | 486 ± 62 |
| High fat feed + prazosin | 368 ± 22 | 916 ± 69 | 740 ± 96 | 584 ± 94 |

*Significantly different from [High fat feed + Vehicle] group ($p < 0.05$)
**Significantly different from [High fat feed + Vehicle] group ($p < 0.01$)
***The maleate of Compound A As is shown in Table 2, the free cholesterol concentration was significantly decreased from 6 weeks after the beginning of the administration in the maleate of Compound A-treated group. On the other hand, no decrease in the free cholesterol concentration in diltiazem-treated group and prazosin-treated group was observed even at 9 weeks after the beginning of the administration.

TABLE 3

Phospholipid concentration in plasma

| Tested Groups | Phospholipid concentration in plasma (mg/dl ± standard error) Test Period (weeks) | | | |
|---|---|---|---|---|
| | 0 | 6 | 8 | 9 |
| Normal feed + Vehicle | 54 ± 2** | 46 ± 1** | 103 ± 8** | 49 ± 3** |
| High fat feed + Vehicle | 461 ± 52 | 1018 ± 98 | 774 ± 82 | 879 ± 144 |
| High fat feed + Compound A*** | 452 ± 42 | 678 ± 70* | 529 ± 66* | 489 ± 60* |
| High fat feed + diltiazem | 454 ± 72 | 931 ± 50 | 825 ± 116 | 718 ± 76 |
| High fat feed + prazosin | 474 ± 22 | 1240 ± 94 | 937 ± 112 | 803 ± 108 |

*Significantly different from [High fat feed + Vehicle] group ($p < 0.05$)
**Significantly different from [High fat feed + Vehicle] group ($p < 0.01$)
***The maleate of Compound A As is shown in Table 3, the phospholipid concentration was significantly decreased from 6 weeks after the beginning of the administration in the maleate of Compound A-treated group. On the other hand, no decrease in the phospholipid concentration in diltiazem-treated group and prazosin-treated group was observed even at 9 weeks after the beginning of the administration.

TABLE 4

Effects on atherosclerosis

| Tested Groups | Cholesterol amount in aortas (mg/kg of protein) | Area of lipid deposition at aortic inner wall (%)**** |
|---|---|---|
| Normal feed + Vehicle | 19.4 ± 1.8** | 0.0 |
| High fat feed + Vehicle | 373.4 ± 45.1 | 53.6 |
| High fat feed + Compound A*** | 234.4 ± 39.4* | 35.2 |
| High fat feed + diltiazem | 509.3 ± 240.1 | 45.2 |
| High fat feed + prazosin | 372.8 ± 63.9 | 56.7 |

*Significantly different from [High fat feed + Vehicle] group ($p < 0.05$)
**Significantly different from [High fat feed + Vehicle] group ($p < 0.01$)
***The maleate of Compound A
****The percentage of lipid deposition area to the whole area of aortic inner wall As is shown in Table 4 and FIG. 1, the cholesterol amount in the aorta in [High fat feed+Vehicle] group was significantly increased as compared with that of [Normal Feed] group, and the area of lipid deposition at the aortic inner wall was almost 54% of the total area of the aortic inner wall. On the contrary, the cholesterol amount in the aorta in the maleate of Compound A-treated group was significantly decreased, and the area of lipid deposition was also decreased. On the other hand, neither the cholesterol amount in the aorta nor the area of lipid deposition at the aortic inner wall in the diltiazem-treated group and prazosin-treated group was not decreased at all.

From the above results, it is proved that Compound A and a pharmaceutically acceptable salt thereof have the hyperlipidemia inhibitory activity (Tables 1 to 3) and the atherosclerosis inhibitory activity (Table 4, FIG. 1), by which they are an excellent agent for ameliorating blood lipid metabolism.

EXAMPLES

The present invention is illustrated by Examples for preparing the pharmaceutical preparations.

Example 1

Preparation of Tablets

| Formula; | |
|---|---|
| Maleate of Compound A | 30 mg |
| Lactose | 55 mg |
| L-HPC | 30 mg |
| HPC-L | 3 mg |
| Crystalline Cellulose | 26 mg |
| Talc | 5 mg |
| Light silicic anhydride | 1 mg |
| Total | 150 mg/tablet |

Method;

The prescribed amounts of maleate of Compound A, lactose and L-HPC are combined, and the mixture is granulated by wet granulation. To the granules are added the remaining components, and the mixture is tabletted to give tablets.

Example 2

Preparation of powders

| Formula; | |
|---|---|
| Maleate of Compound A | 20 g |
| HPMC | 60 g |
| Lactose | 760 g |
| L-HPC | 160 g |

Method;

Maleate of Compound A and HPMC are dissolved in a mixture (2000 ml) of dichloromethane and ethanol (1:1), and the mixture is sprayed to the mixture of lactose and L-HPC by using a fluidized granulator, and the mixture is dried to give powders.

Industrial Applicability

The agent of the present invention is useful as an ameliorant for blood lipid metabolism, especially as a hyperlipidemia inhibitor and atherosclerosis inhibitor, in mammals including human beings.

We claim:

1. A method for ameliorating blood lipid metabolism in a mammal with a blood lipid metabolism disorder, which comprises administering to said mammal a therapeutically, effective amount of a compound having the structure

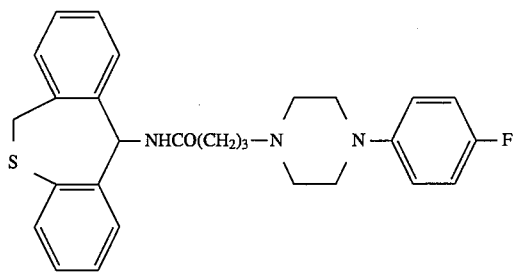

or a pharmaceutically acceptable salt thereof.

2. The method according to claim 1, which inhibits hyperlipidemia.

3. The method according to claim 1, which inhibits atherosclerosis.

4. A method for treating hyperlipidemia in a mammal in need of such treatment comprising administering to said mammal a hyperlipidemia inhibiting effective amount of a compound having the structure

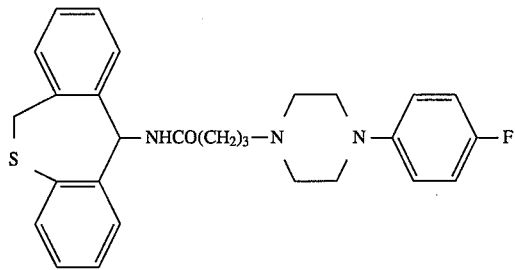

or a pharmaceutically acceptable salt thereof.

5. The method according to claim 4 wherein the pharmaceutically acceptable salt of said compound is administered to the mammal.

6. The method according to claim 5 wherein the pharmaceutically acceptable salt is the pharmaceutically acceptable acid addition salt of said compound.

7. The method according to claim 6 wherein the pharmaceutically acceptable salt is the maleate of said compound.

8. The method according to claim 4 wherein the mammal is a human being.

9. A method for treating atherosclerosis in a mammal in need of such treatment comprising administering to said mammal an atherosclerosis inhibiting effective amount of a compound having the structure

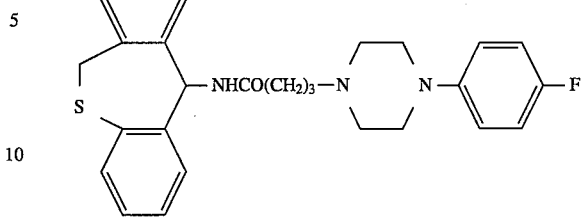

or a pharmaceutically acceptable salt thereof.

10. The method according to claim 9 wherein the pharmaceutically acceptable salt of said compound is administered to the mammal.

11. The method according to claim 10 wherein the pharmaceutically acceptable salt is the pharmaceutically acceptable acid addition salt of said compound.

12. The method according to claim 11 wherein the pharmaceutically acceptable salt is the maleate of said compound.

13. The method according to claim 9 wherein the mammal is a human being.

14. The method according to claim 1 wherein the therapeutically effective amount is a hyperlipidemia inhibiting effective amount or atherosclerosis inhibiting effective amount.

15. The method according to claim 1 wherein the pharmaceutically acceptable salt of said compound is administered to the mammal.

16. The method according to claim 15 wherein the pharmaceutically acceptable salt is the pharmaceutically acceptable acid addition salt of said compound.

17. The method according to claim 16 wherein the pharmaceutically acceptable salt is the maleate of said compound.

18. The method according to claim 1 wherein the mammal is a human being.

* * * * *